& Mathis

United States Patent [19]

Yamamoto et al.

[11] Patent Number: 4,705,628

[45] Date of Patent: Nov. 10, 1987

[54] IMMUNOGLOBULIN ADSORBENT AND ADSORPTION APPARATUS
[75] Inventors: Yuichi Yamamoto; Tadashi Sameshima, both of Fujinomiya, Japan
[73] Assignee: Terumo Kabushiki Kaisha, Tokyo, Japan
[21] Appl. No.: 849,068
[22] Filed: Apr. 7, 1986
[30] Foreign Application Priority Data

Apr. 9, 1985 [JP] Japan .................................. 60-75148
[51] Int. Cl.[4] ............................................ B01D 15/00
[52] U.S. Cl. .............................. 210/289; 210/502.1; 502/402
[58] Field of Search ................... 436/524, 527, 532; 502/402; 548/197, 246, 138; 210/287, 289, 502.1, 927, 506, 908

[56] References Cited

U.S. PATENT DOCUMENTS

| 4,001,583 | 1/1977 | Barrett ........................ 436/532 X |
| 4,059,685 | 11/1977 | Johnson ....................... 436/532 X |
| 4,202,775 | 5/1980 | Abe et al. ..................... 210/927 X |
| 4,321,363 | 3/1982 | Takiguchi et al. . |
| 4,384,954 | 5/1983 | Nakashima et al. ......... 210/502.1 X |
| 4,409,105 | 10/1983 | Hayashi et al. .................... 502/402 |
| 4,420,395 | 12/1983 | Tanihara et al. ............ 210/502.1 X |
| 4,430,229 | 2/1984 | Yamawaki et al. .......... 210/502.1 X |
| 4,432,871 | 2/1984 | Yamawaki et al. . |
| 4,472,303 | 9/1984 | Tanihara et al. ............... 210/927 X |

FOREIGN PATENT DOCUMENTS

| 0059598 | 9/1982 | European Pat. Off. . |
| 0064378 | 11/1982 | European Pat. Off. . |
| 2384789 | 10/1978 | France . |
| 218189 | 1/1985 | German Democratic Rep. ........................... 436/527 |
| 55-120875 | 9/1980 | Japan . |
| 55-125872 | 9/1980 | Japan . |
| 57-77624 | 5/1982 | Japan . |
| 57-77625 | 5/1982 | Japan . |
| 57-134164 | 8/1982 | Japan . |
| 57-156035 | 9/1982 | Japan . |
| 57-170263 | 10/1982 | Japan . |
| 57-197294 | 12/1982 | Japan . |
| 58-61752 | 4/1983 | Japan . |
| 58-98142 | 6/1983 | Japan . |
| 58-133257 | 8/1983 | Japan . |
| 58-165859 | 9/1983 | Japan . |
| 58-165861 | 9/1983 | Japan . |
| 186559 | 10/1984 | Japan ........................... 436/524 |
| WO83/02669 | 8/1983 | PCT Int'l Appl. . |
| 2075362 | 11/1981 | United Kingdom ............... 210/927 |
| 2092470 | 8/1982 | United Kingdom . |

OTHER PUBLICATIONS

Sieberth, H. G., "The Elimination of Defined Substances from the Blood and from Separated Plasma, *Plasma Exchange*-International Symposium in Cologne, Jun. 6 and 7, 1980.
Tetsuzo Agishi, et al., *Kidney and Dialysis*, vol. 10 (3), p. 475 (1981).
Ohe, H., et al., *Artificial Organs*, vol. 14 (1), p. 472 (1985).
L'Abbate, A., et al., "Selective Removal of Plasma Cryoglobulins in Cryoglobulinaemia", *Proc. Eur. Dial. Transport Assoc.*, vol. 14, pp. 486–494 (1977).

*Primary Examiner*—Richard V. Fisher
*Assistant Examiner*—W. Gary Jones
*Attorney, Agent, or Firm*—Burns, Doane, Swecker & Mathis

[57] ABSTRACT

For the treatment of various diseases including autoimmune diseases such as myathenia gravis, articular rhematism, lupus erythematosus, etc., immunity-related diseases such as glumerulonephritis, bronchial asthma, polyneuritis, etc., organ transplantation such as transplanted kidney rejection, AOB incompatibility bone marrow transplantation, etc., tumor, hypertension, and hepatic insufficiency, immunoglobulin adsorbents comprising a hydroxyl-containing water-insoluble carrier to which a diamine compound having the general formula:

$$NH_2(CH_2)_nNH_2$$

wherein n is an integer having a value of 3 to 9 is attached through a silane coupling agent or a derivative thereof, to which diamine a heterocyclic compound is attached through a difunctional reagent, are useful as they can selectively and efficiently adsorb specific proteins such as immunoglobulins and immune complexes which are pathogenic substances in the diseases, exhibit minimized non-specific adsorption, and are safe and easy to sterilize.

17 Claims, 4 Drawing Figures

IMMUNOGLOBULIN ADSORBENT AND ADSORPTION APPARATUS

BACKGROUND OF THE INVENTION

This invention relates to immunoglobulin adsorbents and apparatus for adsorbing immunoglobulins using such adsorbents useful in the treatment of various diseases including autoimmune diseases such as myathenia gravis, articular rheumatism, lupus erythematosus, etc., immunity-related diseases such as glumerulonephritis, bronchial asthma, polyneuritis, etc., organ transplantation such as transplanted kidney rejection, AOB incompatible bone marrow transplantation, etc., tumor, hypertension, and hepatic insufficiency.

In recent years, plasma exchange therapeutics have been employed for the purpose of treating autoimmune diseases, immunity-related diseases, organ transplantation, tumor, hypertension, hepatic insufficiency and other diseases. In the plasma exchange therapeutics, however, all the plasma components are indiscriminately removed so that useful components in plasma are lost. Several problems are pointed out including shortness of useful components in plasma or plasma preparations used as a make-up and probable complication of serum hepatitis and allergy. It is thus believed desirable to depurate the patient's own plasma before it is transfused.

A variety of methods have been devised for removal of pathogenic substances, for example, cascade method using a membrane filter (see H. G. Sieberth, Plasma Exchange, p. 29, F. K. Schattauer Verlag, Stuttgart-New York, 1980), double filtration (see, Tetsuzo Agishi et al., Kidney and Dialysis, 10(3), 475, 1981), freeze filtration (A. L'Abbate et al., Proc. Eur. Dial. Transplant. Assoc., 14, 486, 1977), and plasma salting-out treatment (see, Oe Hiroaki et al., Artificial Organs, 14(1), 472, 1985). These methods are on the way of clinical trial.

However, removal of unnecessary pathogenic substances is insufficient under the current circumstances. Clinical application will invite hypoproteinemia unless plasma make-up is used.

Other therapeutics are by the use of various medicines. Because of probable side-effects, a careful attention must be paid to their use. For example, their dose and administration period should be limited as low as possible.

There is the need for a depurant and depuration apparatus capable of selectively adsorbing and removing particular pathogenic substances in plasma without inducing a side-effect. There are known a number of depurants for such purposes, including (1) affinity adsorbents,
(2) porous resins such as Amberite XAD-7 sold by Rohm & Haas,
(3) ion-exchange materials such as carboxymethyl cellulose and diethylaminoethyl agarose, and
(4) porous inorganic materials such as porous glass and ceramics.

However, these depurants have several drawbacks. The porous resins and ion-exchange materials have low adsorptivity and poor adsorption specificity. They also adsorb albumin in body fluid to induce an anomalous change in osmotic pressure so that they cannot be used as a safe therapeutic member. The porous inorganic materials are not yet sufficient for practical use despite their relatively high adsorptivity and adsorption specificity.

The affinity adsorbents are generally classified into biological and physicochemical affinity adsorbents. The biological affinity adsorbents exhibit excellent adsorption specificity. However, most biological affinity adsorbents use a physiologically active high molecular weight compound as a ligand (material having affinity to a target material) and are thus expensive and difficult to gain. It is difficult to maintain the activity during preparation of adsorbents and columns, sterilization, stock storage, transportation, and shelf storage. A side effect must be taken into account because the biological affinity adsorbents can exert physiological functions other than affinity upon contact with blood. There is the likelihood that the ligand be released or dissolved away. Since most ligands are heterogeneous proteins, there occurs a problem of side effect due to antigenicity. On the other hand, the physicochemical affinity adsorbents have the advantages that they can be produced in a mass scale and their activity is stable. There are many physicochemical affinity adsorbents which are highly safe when contacted with blood.

A number of such adsorbents are known in the art, for example, porous materials having carboxyl group or sulfonate group at the surface as disclosed in Japanese Patent Application Kokai Nos. 56-147710, 57-56038, 57-75141, 57-170263, and 57-197294; hydrophilic carriers having a hydrophobic amino acid attached thereto as disclosed in Japanese Patent Application Kokai Nos. 57-122875, 58-15924, 58-165859, and 58-165861; hydrophilic carriers having denatured IgG attached thereto as disclosed in Japanese Patent Application Kokai Nos. 57-77624, 57-77625, and 57-156035; porous materials having methylated albumin attached thereto as disclosed in Japanese Patent Application Kokai Nos. 55-120875 and 55-125872; hydrophilic carriers having saccharide attached thereto as disclosed in Japanese Patent Application Kokai Nos. 57-134164 and 58-133257; and porous materials having purine base or pyrimidine base or saccharide phosphate attached thereto as disclosed in Japanese Patent Application Kokai Nos. 57-192560, 58-61752, and 58-98142. In order to carry out extracorporeal circulation body fluid depuration therapy for the treatment of diseases, there is the need for an adsorbent which can more efficiently remove pathogenic substances than these prior art adsorbents while having less or little adverse effect on body fluid.

SUMMARY OF THE INVENTION

Therefore, an object of the present invention is to provide a novel and improved immunoglobulin adsorbent which can selectively and efficiently adsorb specific proteins such as immunoglobulins and immune complexes which are pathogenic substances in diseases related to living body immunity function such as autoimmune diseases, allergy, and cancer, exhibits minimized non-specific adsorption, and is safe and easy to sterilize.

Another object of the present invention is to provide an immunoglobulin adsorbing apparatus using the improved adsorbent.

According to a first aspect of the present invention, there is provided an adsorbent for an immunoglobulin comprising a hydroxyl-containing water-insoluble carrier. A diamine compound having the general formula:

$$NH_2(CH_2)_nNH_2$$

wherein n is an integer having a value of 3 to 9, such as a diamine selected from the group consisting of 1,3-propanediamine, 1,6-hexanediamine, and 1,9-diaminononane is attached to the carrier through a silane coupling agent or a derivative thereof. A heterocyclic compound is further attached to the diamine through a difunctional reagent.

Preferably, the difunctional reagent is a difunctional reagent capable of bonding amino groups with each other and said heterocyclic compound is a heterocyclic compound having an amino group or having an amino group incorporated therein.

Preferably, the heterocyclic compound is a sulfa drug in the form of a sulfonamide.

Preferably, the silane coupling agent is selected from the group consisting of γ-glycidoxypropyltrimethoxysilane, γ-glycidoxypropylmethyldiethoxysilane, β-(3,4-epoxycyclohexyl)-ethyltrimethoxysilane, γ-aminopropyltriethoxysilane, and N-β(aminoethyl)-γ-aminopropyltrimethoxysilane.

Preferably, the difunctional reagent is selected from the group consisting of dialdehydes, bisepoxides, alkylimide esters, and diisocyanates. The most preferred difunctional reagent is glutaraldehyde.

Preferably, the sulfa drug is selected from the group consisting of sulfathiazole, sulfamethizole, and sulfisomezole.

Preferably, the water-insoluble carrier is comprised of a porous inorganic material predominantly comprising silicon dioxide and having a silanol group. Preferably, it is in the form of particles having a particle diameter in the range between 0.05 mm and 5 mm and a mean pore diameter between 1000 angstrom and 5000 angstrom.

According to a second aspect of the present invention, there is provided an apparatus for adsorbing an immunoglobulin comprising a vessel having an inlet and an outlet for passing body fluid therethrough, an adsorbent charged in said vessel, the adsorbent being as defined above, and means for preventing the adsorbent from flowing out of the vessel.

Preferably, a filter disposed in the vessel as the means for preventing the adsorbent from flowing out of the vessel.

BRIEF DESCRIPTION OF THE DRAWINGS

These and other objects, features, and advantages of the present invention will be seen by reference to the description, taken in connection with the accompanying drawings, in which.

DETAILED DESCRIPTION OF THE INVENTION

Figure 1:
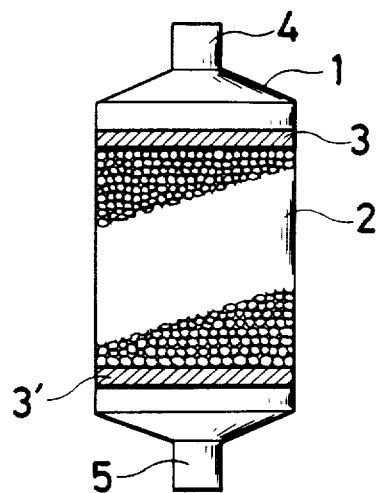
FIG. 1 is a schematic view in cross section of an immunoglobulin adsorbing apparatus according to the present invention.

The present invention in its first aspect provides an adsorbent for an immunoglobulin comprising a hydroxylcontaining water-insoluble carrier to which a diamine compound having the general formula:

$$NH_2(CH_2)_nNH_2$$

wherein n is an integer having a value of 3 to 9 is attached through a silane coupling agent or a derivative thereof, with a heterocyclic compound being attached to the diamine through a difunctional reagent.

The substances that are to be adsorbed and removed in the practice of the present invention are broadly proteins contained in body fluid and more precisely, common immunoglobulins, IgA, IgD, IgE, IgG, and IgM, autoantibodies, complexes between immunoglobulins, and complexes between an immunoglobulin and another substance, particularly an antigen as shown in Table 1. For brevity of description, these substances are generally referred to as pathogenic substances, hereinafter.

TABLE 1

| Autoimmune diseases and autoantibodies (based on the classification by Roitt)* | |
|---|---|
| Autoimmune diseases | Autoantibodies |
| Class I (Organ-specific) | |
| Hashimoto's disease, Primary myxedema | antithyroglobrin antibody, secondary colloid antibody, cytoplasmic microsome antibody, cell surface antibody |
| thyrotoxicosis | antibody for TSH receptor on thyroid cell surface |
| Pernicious anemia, atrophic gastritis | intrinsic factor, gastric parietal cell microsome antibody |
| Addison's disease | adrenocortical cytoplasmic antibody |
| orchtis, male infertility | spermatozoa antibody |
| climacterium precox | steroid-producing interstitial cytoplasmic antibodies of adrenal, ovary and testis |
| multiple sclerosis | brain cell antibody |
| Class II (intermediate) | |
| Goodpasture's syndrome | glomerular and alveolar basement membrane antibodies |
| glomerulonephritis | glomerular basement membrane antibody |
| myasthenia gravis | antibody for acetylcholine receptor |
| pemphigus vulgaris | epidermic inter-spine-cellular desmosome antibody |
| pemphigoid | skin basement membrane antibody |

TABLE 1-continued

Autoimmune diseases and autoantibodies
(based on the classification by Roitt)*

| Autoimmune diseases | Autoantibodies |
|---|---|
| lens-induced uveitis | corpus vitreum antibody |
| sympathetic ophthalmia | uveal antibody |
| antoimmune hemolytic aneria | erythrocyte antibody |
| idiopathic thrombocytopenic purpura | platelet antibody |
| primary biliary cirrhosis | mitochondria antibody |
| active chronic hepatitis | smooth muscle antibody, antinuclear antibody |
| ulcerative colitis | colon lipopolysaccharide antibody |
| Sjogren's syndrome | salivary duct antibody, mitochondria antibody, antinuclear antibody thyroid antibody, anti-IgG antibody |
| polyneuritis | myelinic antibody |
| juvenile diabetes | insulin receptor antibody |
| Class III (Non-organ-specific) | |
| systemic lupus erythematosus (SLE) | DNA antibody, nucleoprotein antibody, antibodies in non-liquid components of blood, coagulation factor antibody, denatured IgG antibody, Wassermann's antigen antibody |
| discoid lupus erythematosus (DLE) | antinuclear antibody, anti-IgG antibody |
| dermatomyositis, scleroderma, chronic rheumatism | anti-IgG antibody (Rheumatoid factor), antinuclear antibody |

*Tsuruta & Sakurai Ed., Biomaterial Science Vol. 2, Nankodo, Tokyo, 1982

The heterocylic compounds used in the practice of the present invention are cyclic compounds having one or more heteroatoms along with carbon atoms in the ring. They include five-membered heterocylic compounds such as furan and its derivatives, thiophene and its derivatives, dithiolan and its derivatives, pyrrole and its derivatives, and azoles; six-membered heterocylic compounds such as pyridine and its derivatives, quinoline and related compounds, pyrazine and related compounds, pyran and pyrone and their related compounds, phenoxadine, phenothiadine, pteridine and alloxazine compounds, purine bases, nucleic acid, hemin, chlorophyll, vitamine B12 and phthalocyanine, or alkaloids and other fused ring heterocyclic compounds. The preferred heterocyclic compounds are chemotherapeutic agents and their derivatives, pyrimidine related compounds, pyridine related compounds, and pyrazine related compounds.

Most preferred among these chemotherapeutic agents and their derivatives, pyrimidine related compounds, pyridine related compounds, and pyrazine related compounds are sulfa agents. Examples of the heterocyclic compounds which are sulfa agents are given below.

List of heterocyclic compounds/sulfa agents

| General name | Structural formula |
|---|---|
| Sulfapyridine | $H_2N$—⌬—$SO_2NH$—⌬—N |
| Sulfathiazole | $H_2N$—⌬—$SO_2NH$—⌬(S,N) |
| Sulfadiazine | $H_2N$—⌬—$SO_2NH$—⌬(N,N) |
| Sulfamerazine | $H_2N$—⌬—$SO_2NH$—⌬(N,N)-$CH_3$ |
| Sulfasuccidine | $CH_2COOH$ / $CH_2CONH$—⌬—$SO_2NH$—⌬(S,N) |
| Sulfamethazine | $H_2N$—⌬—$SO_2NH$—⌬(N,N) with two $CH_3$ |
| Sulfisomidine | $H_2N$—⌬—$SO_2NH$—⌬(N,N) with two $CH_3$ |
| Sulfisoxazole | $H_2N$—⌬—$SO_2NH$—⌬(O,N) with two $CH_3$ |

List of heterocyclic compounds/sulfa agents

| General name | Structural formula |
|---|---|
| Sulfamethizole | H₂N—⟨⟩—SO₂NH—[N=N, S, CH₃ ring] |
| Phthalylsulfathiazole | [⟨⟩ with COOH]—CONH—⟨⟩—SO₂NH—[S,N ring] |
| Sulfadimethoxine | H₂N—⟨⟩—SO₂NH—[pyrimidine with 2 OCH₃] |
| Sulfamonomethoxine | H₂N—⟨⟩—SO₂NH—[pyrimidine with OCH₃] |
| Sulfisomezole | H₂N—⟨⟩—SO₂NH—[isoxazole with CH₃] |
| Sulfamethoxypyridazine | H₂N—⟨⟩—SO₂NH—[pyridazine with OCH₃] |
| Sulfaphenazole | H₂N—⟨⟩—SO₂NH—[pyrazole with phenyl] |

Also included are composites between a sulfa agent and a dye having a pK value of 4.0 to 9.0, 2-thiouracil, isonicotinic acid hydrazide, and luminol. Illustrative examples of the dyes having pK 4.0 to 9.0 are those indicators and histochemical dyes that are described in H. J. Conn's Biological Stains, R. D. Lillie, The Willians & Wilkins Company, Baltimore, 1977, and having a pK value of 4.0 to 9.0. It is preferred that the dyes have a pK value approximately equal to the isoelectric point of a pathogenic substance. Thus the preferred dyes have the above-defined pK range.

Some illustrative non-limiting examples of the dyes are shown below.

Lacmoid
7-amino-3,6-bis(m-dihydroxy-phenyl)-2-phenexazone

Brilliant yellow

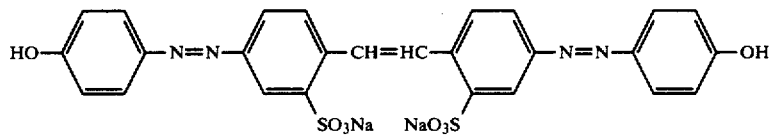

Phenol red
(4,4'-(3H-2,1-benzoxathiol-3-ylidene),*bisphenol s,s'-dioxide

The sulfa agents and the compounds of sulfa agents combined with dyes having pK 4.0–9.0 ensure better results when the sulfa agent is selected from sulfathiazole, sulfamethizole, and sulfisomezole, and the dye having pK 4.0–9.0 is selected from Lacmoid, Brilliant yellow, and Phenol red. These sulfa agents are $N^1$-heterocyclic compounds whose hetero-rings belong to the azole family, and more specifically, they are thiazole, 2-methylthiadiazole, and 2-methylisoxazole.

The hetero-atoms of the pyridines, pyrimidines and azoles which are the preferred heterocyclic compounds used in the practice of the present invention have a lone pair and act as a proton acceptor. Hetero-rings having less dissociation groups exhibit hydrophobic properties. The sulfonamide moiety of the sulfa agents, the thiol or hydroxyl group of 2-thiourecil, the acid amide moiety of isonicotinic acid hydrazide, and the carbonyl and imino groups of luminol have hydrogen bondability. It is thus interpreted that preferred results are obtained in the adsorption of pathogenic substances, particularly globulin substances by the heterocyclic compounds because the hydrophobic properties of a predominant portion of the heterocyclic compounds, the electrostatic properties of the hetero-atoms, and the hydrogen bondability near the predominant portion all make interactions with amino acid residues of the globulin compounds at the site to be adsorbed and the stereo structure of the heterocylic compounds adequately mates with an intramolecular pocket of the globulin compounds.

In connection with the above-mentioned mechanism, it is believed that a variety of interactions are involved in the adsorption of pathogenic substances by the adsorbents of the present invention. Typical interactions involved include:
(1) hydrophobic bonding,
(2) electrostatic bonding,
(3) hydrogen bonding,
(4) van der Waals-London interactions,
(5) coordination bonding, and
(6) steric adaption.

The heterocylic compounds may generally be fixed to the surface of the insoluble carriers by utilizing a covalent bond, an ionic bond, physical adsorption, embedding, and settlement on the carrier surface followed by insolubilization. The use of a covalent bond is preferred when the stability of a ligand in body fluid is taken into account.

In order to covalently bond the heterocyclic compound to the surface of the insoluble carrier, any desired coupling agents may be used depending on the functional groups on both of them. More illustratively, the hydroxyl group of the insoluble carrier may be covalently bonded to the amino group of the heterocyclic compound using cyan halides such as cyan bromide, halo-triazines, bromoacetyl bromide, epihalohydrins such as epichlorohydrin, bisepoxides such as 1,4-butanediol-diglycidyl ether, and silane coupling agents such as γ-glycidoxypropyltrimethoxysilane (GOPTS).

Because of ease of handling, silane coupling agents are selected herein as the coupling agents which can readily form a covalent bond with the insoluble carriers having a hydroxyl group and form a stable covalent bond with the heterocyclic compounds having an active hydrogen-containing functional group such as an amino, hydroxyl, thiol, and carboxyl group under moderate conditions.

Some illustrative non-limiting examples of the silane coupling agents include
γ-glycidoxypropyltrimethoxysilane (GOPTS),
γ-glycidoxypropylmethyldiethoxysilane having the formula:

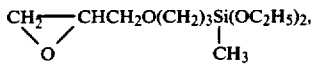

β-(3,4-epoxycyclohexyl)ethyltrimethoxysilane having the formula:

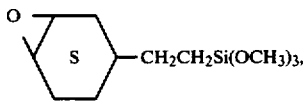

γ-aminopropyltriethoxysilane having the formula:

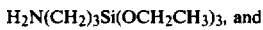

N-β(aminoethyl)-γ-aminopropyltrimethoxysilane having the formula:

It should be understood that the last two compounds have a terminal organic functional group in the form of an amino group must be bonded to a terminal amino group of a spacer as will be described later, with glutaraldehyde or the like. The most preferred silane coupling agent is γ-glycidoxypropyltrimethoxysilane (GOPTS).

In affinity chromatography, when an affinity ligand attached to an insoluble carrier bonds with a target substance in a specific and reversible manner, the length and type of a spacer or intermediate carbon chain for supporting the ligand are important. P. O'Carra et al. reports that the length and type of a spacer are important factors and an extremely long spacer bonds with a substance in a sample via hydrophobic interaction. See P. O'Carra et al., Spacer arms in affinity chromatography: the need for a more rigorous approach, Biochem. Soc. Trans., 1(1973), 289–290.

We have made a series of experiments in which the methoxy group of GOPTS was reacted with a hydroxyl group on insoluble carriers, particularly, a hydroxyl group on the surface of silica gels having different pore diameters, then various diamine compounds as a spacer were bonded to the epoxy group of GOPTS, and heterocylic compounds were covalently bonded to the diamine through difunctional reagents. We have found that a diamine compound having the general formula:

wherein n is an integer having a value from 3 to 9 are excellent spacers for use in the immunoglobulin adsorbents of the present invention. The preferred diamine compounds are 1,3-propanediamine, 1,6-hexanediamine, and 1,9-diaminononane. The spacer or ligand becomes too short or long to allow sufficient interactions to occur in the adsorption of a pathogenic substance when n falls outside the range of 3–9.

The difunctional reagents with which the heterocyclic compounds were covalently bonded to the diamine compounds include
dialdehydes such as glutaraldehyde and p-phthaldehyde having the formula:

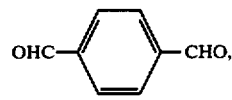

bisepoxides as 1,4-butanediol-diglycidyl ether having the formula:

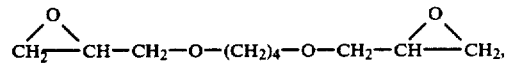

alkylimide esters such as diethylmalonimidate having the formula:

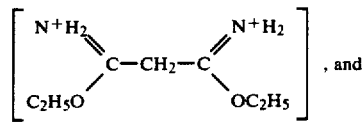

, and diisocyanates such as hexamethylene diisocyanate having the formula:

Most preferred among them is glutaraldehyde.

When the heterocylic compounds as such have not a group capable of reacting with the aldehyde group of glutaraldehyde, an aldehyde-reacting group is previously incorporated in the heterocyclic compounds.

The insoluble carriers used herein preferably possess a hydrophilic surface compatible with water medium and have a hydroxyl group capable of reacting with GOPTS.

In order to efficiently remove pathogenic substances by adsorption, the insoluble carriers are preferably in the form of a porous body having a great surface area. Particularly preferred carriers are inorganic porous bodies predominantly comprising silicon dioxide and having a silanol group because they possess a high mechanical strength and permit autoclave sterilization and because silicon dioxide is available in plenty and thus inexpensive. The preferred carriers are porous bodies. For the purpose of adsorbing and removing IgM having a molecular weight as high as 900,000 and immune complexes having a molecular weight of about 600,000 or higher, the preferred porous bodies have a mean pore diameter in the range between 300 angstrom and 5000 angstrom, more preferably in the range between 1000 angstrom and 3000 angstrom.

Measurement of mean pore diameter is made by means of a mercury porosimeter. Mercury is forcedly penetrated into a porous body. Then the volume of pores is determined by the amount of mercury penetrated and the pore diameter is determined by the pressure required for penetration.

The shape of the insoluble carriers may take any desired known shapes including particulate, fiber, hollow fiber, and membrane shapes. Particulate, especially spherical carriers are preferred because of smooth passage of body fluid and unlikely collapse and chipping.

The particulate carriers preferably have an average particle diameter in the range between 0.05 mm and 5 mm in view of body fluid flow rate and flow pressure. The average particle diameter is calculated by classifying particles through sieves as defined in JIS Z 8801, determining a median between the upper and lower limit particle diameters for each class as a particle diameter for the class, and weight averaging the particle diameters of all the classes.

As previously described with respect to the preferred ligands used in the practice of the present invention, the hetero-atoms of the heterocyclic compounds possess a lone pair in the outermost electron shell and act as a proton acceptor. Hetero-rings having less dissociation groups exhibit hydrophobic properties. The sulfonamide moiety of the sulfa agents have hydrogen bondability.

The spacer for the ligand including the coupling agent segment has a hydroxyl group having hydrogen bondability and exhibits increased hydrophobic property with a longer carbon chain, the length of which is correlated to the area the ligand molecule occupies and to the fitting of the ligand in a specific molecular pocket of a substance to be adsorbed.

On the other hand, the inorganic porous body having the ligand attached thereto has silicon and oxygen atoms of siloxane or hydroxyl groups of silanol at the surface of silicon dioxide based beads and thus possesses hydrogen bondability and electrostatic bondability.

Then, it is believed that in the course of adsorption of a pathogenic substance by an adsorbent, combined interactions of hydrophobic bond, electrostatic bond, and hydrogen bond occur between the amino acid residues of the pathogenic substance and the adsorbent, and the ligand on the adsorbent properly fits in the intramolecule pocket of the pathogenic substance, ensuring favorable results.

In general, adsorbents consisting of hydrophobic compounds have a great amount of useful proteins attached such as albumin in body fluid and are thus unsuitable for the selective removal of pathogenic substances. Inversely, adsorbents consisting of hydrophilic compounds or compounds having many charged groups can have only an extremely small amount of proteins attached so that they are unsuitable for the removal of pathogenic substances. Adsorbents having a proper combination of various interactions are preferred adsorbents for immunoglobulins.

As previously described, various interactions, particularly interactions (1) to (6) are involved in the reaction of the ligand with a material to be adsorbed or immunoglobulin (Ig). The length of the ligand has a significant influence on these interactions.

As the methylene chain of the spacer, diamine compound in the present invention, in the ligand increases its length, the spacer exhibits increased hydrophobic properties, that is, hydrophobic bonding (1) is enhanced. The length of the ligand is closely related to steric adaption (6) and determines whether the distal end of the ligand can contact amino acid residues in the deep of the pocket of Ig. When the methylene chain of the spacer or diamine compound is represented by $(CH_2)_n$, the length of the ligand, that is, the sum of the lengths of silane coupling agent, diamine compound, and heterocyclic compound has the following approximate value in angstrom calculated from atomic distance.

$C_0$:29
$C_3$:44
$C_6$:49
$C_9$:53
$C_{12}$:58

Likewise, the length of the diamine compounds has the following value in angstrom.

$C_3$:9
$C_6$:14
$C_9$:18
$C_{12}$:23

Thus, preferably the diamine compounds have a length of from about 5 to about 20 angstrom and the ligands have a length of from about 40 to about 55 angstrom. Sufficient interactions do not occur when the diamine compounds and the ligands have lengths outside the above-specified ranges.

The immunoglobulin adsorbing apparatus of the present invention includes a vessel having an inlet and an outlet for the passage of body fluid therethrough. The adsorbent as defined above is charged and retained in the vessel.

The materials of which the vessel is made may include glass, stainless steel, polyethylene, polypropylene, polycarbonate, polystyrene, polymethylmethacrylate, etc. with the polypropylene and polycarbonate being preferred because of autoclave sterilization and ease of handling. The vessel is further provided with means for preventing the adsorbent from flowing out of the vessel. Illustratively, a filter is disposed between the adsorbent and the inlet and outlet which has a screen mesh or opening sufficient to allow passage of body fluid, but prevent passage of the adsorbent. The filter may be formed of any desired materials as long as they are physiologically inert and mechanically strong. The preferred filters are of mesh polyester and polyamide.

Referring to FIG. 1, there is illustrated in cross section a preferred embodiment of the immunoglobulin adsorbing apparatus of the present invention.

The apparatus includes a cylindrical vessel 1 having an inlet 4 and an outlet 5 for the passage of body fluid. A mass of immunoglobulin adsorbent 2 is charged in the vessel 1 and retained between a pair of filters 3 and 3' disposed in the vessel near the inlet 4 and the outlet 5. Body fluid is introduced into the vessel 1 via the inlet 4, passed through the adsorbent mass for treatment, and discharged through the outlet 5.

Figure 2:
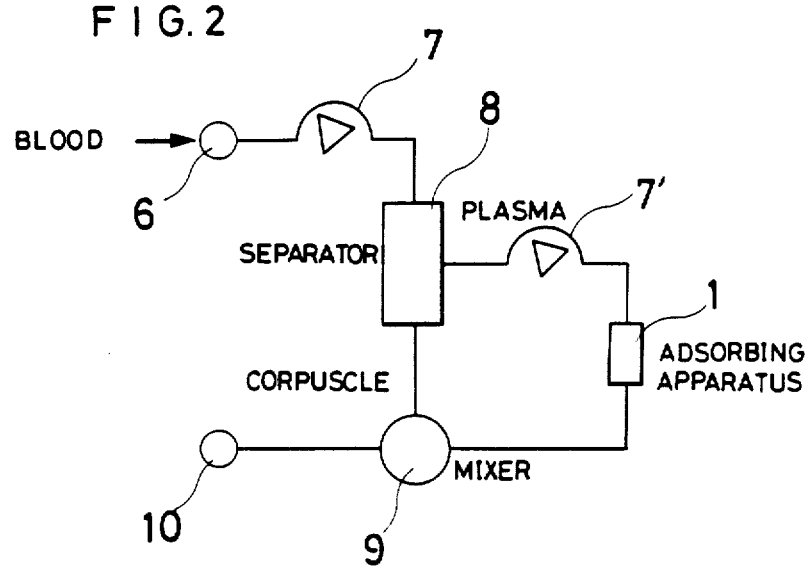
FIG. 2 is a block diagram showing a hemocatharsis system using the apparatus of the present invention.

FIG. 2 illustrates a hemocatharsis system. Blood is pumped from an inlet 6 by means of a pump 7 to a plasma separator 8 where it is separated into plasma and corpuscle components. The separated plasma is fed to the immunoglobulin adsorbing apparatus 1 shown in FIG. 1 by means of a pump 7' where it is subjected to adsorption. The treated plasma is combined with the corpuscle component in a plasma-corpuscle mixer 9 and then fed to a desired destination via an outlet 10.

EXAMPLES

Examples of the present invention are given below along with comparative examples. GOPTS means gamma-glycidoxypropyltrimethoxysilane and DMF means dimethylformamide. Water used is distilled water.

EXAMPLE 1 AND COMPARATIVE EXAMPLE 1

Porous silica gel beads (manufactured by Fuji-Davidson Chemical K.K.) having a particle diameter in the range from 74 to 149 μm and different pore diameters of 324, 460, 685, 906, 971, and 2361 Å as shown in Table 2 were immersed in a 5 w/v % GOPTS aqueous solution which had been adjusted to pH 9 with potassium hydroxide. A heat treatment was effected to cause a silanol group on the surface of silica gel to react with the methoxy group of GOPTS to produce a GOPTS-grafted silica gel. This process is represented by reaction scheme 1.

The GOPTS-grafted silica gel was added to a distilled water ($H_2O$)-DMF solution of 0.1 M diamine compound, namely 1,3-propanediamine, 1,6-hexanediamine and 1,9-diaminononane which are within the scope of the present invention, dodecamethylenediamine and p-phenylenediamine which are outside the scope of the present invention. After deaeration and addition of pyridine and tri-n-butylamine catalysts, the reaction mixture was warmed to cause the epoxy group of GOPTS to react with the amino group of the diamine compound. Reaction scheme 2 represents the process wherein the amine compound used is 1,3-propanediamine.

The reaction product was washed with water and DMF, and then immersed in an aqueous solution of 5 v/v % glutaraldehyde. After deaeration, the mixture was adjusted to pH 7 with sodium hydroxide and agitated at room temperature to effect the reaction. The product was washed with water. This process is represented by reaction scheme 3.

The reaction product was immersed in a solution of 0.1 M a heterocyclic compound as shown in Table 2 in a 2:3 (by volume) mixed solution of DMF and pH 8/10 mM calcium chloride aqueous solution. The reaction mixture was deaerated to remove air in the pores and then agitated at room temperature to effect the reaction. Reaction scheme 4 represents the process wherein sulfathiazole is employed as the heterocyclic compound.

The reaction product was washed with water and DMF, and then immersed in an aqueous solution of 1 M ethanol amine for blocking the unreacted epoxy and/or aldehyde groups. The mixture was deaerated and allowed to react at room temperature.

The reaction product was washed with water. Then, an optional treatment, for example, reducing treatment was effected to stabilize the bond resulting from the reaction between the aldehyde group of glutaraldehyde and an aldehydereacting group such as an amino group of the heterocyclic compound.

When sulfathiazole was used as in reaction scheme 4, for example, the reaction product was immersed in a solution of 1 w/v % sodium boron hydride in pH 8/10 mM calcium chloride solution to reduce the azomethin bond resulting from the reaction between the amino group of sulfathiazole and the aldehyde group of glutaraldehyde. This process is represented by reaction scheme 5.

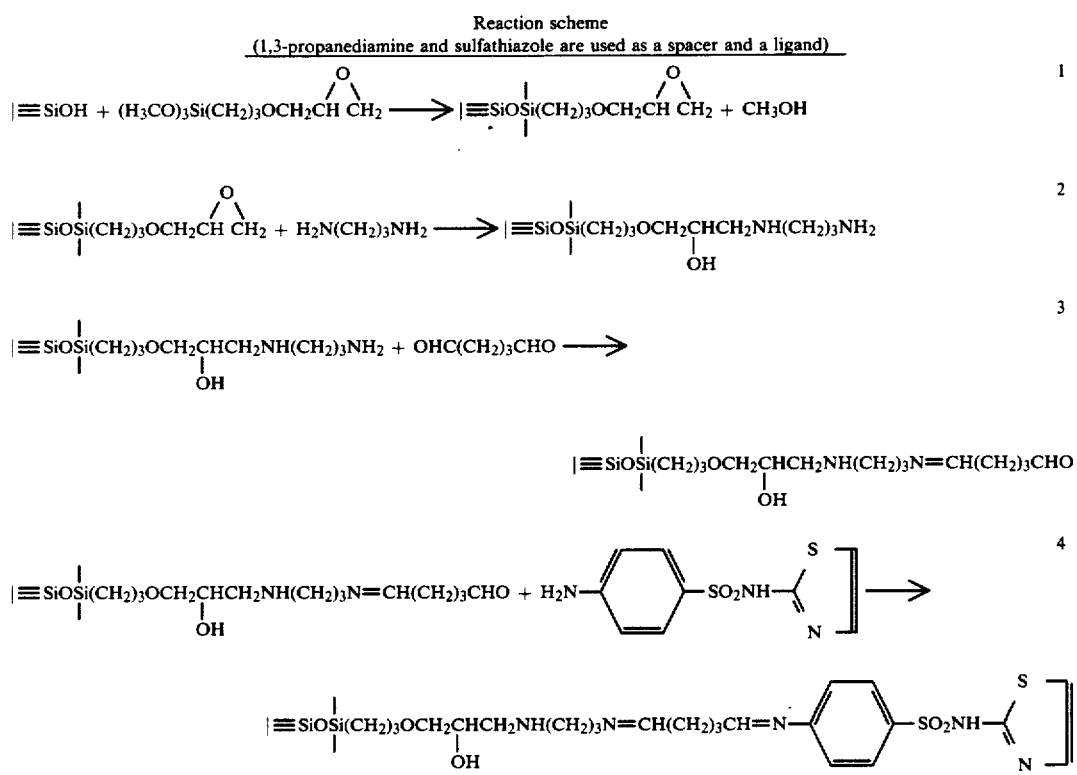

-continued
Reaction scheme
(1,3-propanediamine and sulfathiazole are used as a spacer and a ligand)

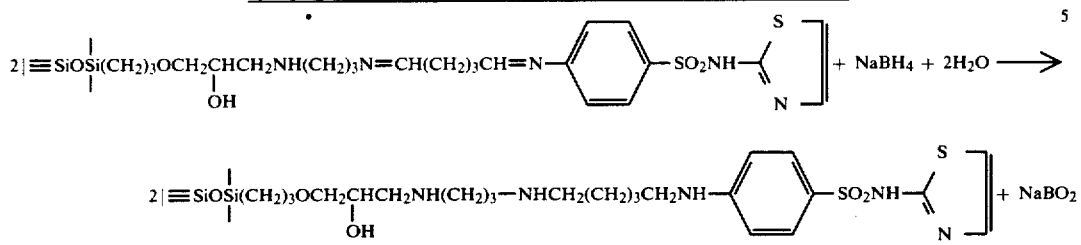

The product was repeatedly washed with water, a pH 4/0.02 M acetate buffer solution containing 0.5 M sodium chloride, and a pH 10/0.2 M carbonate buffer solution, further washed with acetone, and dried at 120° C. for 2 to 3 hours under vacuum. Samples weighing 1 gram were taken from the dry product and placed in glass tubes of 15.5 mm diameter ×100 mm long (Larbo ®, manufactured by Terumo K.K.). These adsorbents were tested for adsorption performance.

For comparison purposes, there were prepared untreated silica gel beads having no ligand and spacer-free adsorbents, that is, GOPTS-grafted silica gels wherein the epoxy group of GOPTS was directly reacted with heterocyclic compounds (as shown in Table 2) without a spacer. One gram samples of them were subjected to a similar adsorption test.

The adsorption test was carried out by adding 3 ml of pH 7.2/8 mM phosphate buffer solution (PBS) containing 137 ml sodium chloride and 2.6 mM potassium chloride to the test tube charged with the adsorbent. After deaeration with an aspirator (A-2S type, manufactured by Tokyo Rikakiki K.K.), 3 ml of bovine plasma containing 6 IU/ml heparin as an anticoagulant and 50 μl /ml ACD was added to the tube. The soaked adsorbent was incubated at 37° C. for 90 minutes in a warm air circulating incubator (P(S)-212 type, manufactured by Tabai K.K.) with stirring by a blood mixer (BM-101 type, manufactured by Kayagaki Irika Kogyo K.K.). The contents of the reaction tube were transferred to a small column in the form of a 5-ml volume disposable syringe (manufactured by Terumo K.K.) with the aid of 1 ml PBS. The column was washed with 5 ml PBS and the eluent was collected and metered. The quantity of immunoglobulin M (IgM) was determined by a simple radial immunodiffusion (SRID) technique. This value was subtracted from the net quantity of IgM in the eluent obtained by repeating a similar procedure without using the adsorbent, to determine the quantity of IgM adsorbed by the adsorbent. Percent adsorption was calculated by dividing the quantity of IgM adsorbed by the net quantity of IgM in the eluent obtained without the adsorbent.

The results are shown in Table 2. Based on these data, the percent IgM adsorption is plotted in FIGS. 3 and 4 as a function of the average pore diameter of carriers when the heterocyclic compound used was sulfathiazole.

TABLE 2

| (Bovine plasma) | | | |
|---|---|---|---|
| Heterocyclic compound | Spacer | Carrier average pore diameter, Å | IgM adsorption |
| Examples | | | |
| sulfathiazole | 1,3-propanediamine | 324 | 6.7 |

TABLE 2-continued

| (Bovine plasma) | | | |
|---|---|---|---|
| Heterocyclic compound | Spacer | Carrier average pore diameter, Å | IgM adsorption |
| | | 460 | 13.9 |
| | | 685 | 21.1 |
| | | 971 | 35.9 |
| | | 2361 | 46.6 |
| sulfathiazole | 1,6-hexanediamine | 324 | 6.9 |
| | | 460 | 14.1 |
| | | 685 | 22.5 |
| | | 971 | 27.2 |
| | | 2361 | 34.1 |
| sulfathiazole | 1,9-diaminononane | 324 | 0 |
| | | 460 | 10.8 |
| | | 685 | 18.8 |
| | | 971 | 16.0 |
| | | 2361 | 34.6 |
| Comparative Examples | | | |
| sulfathiazole | dodecamethylenediamine | 324 | 4.9 |
| | | 460 | 11.5 |
| | | 685 | 19.8 |
| | | 971 | 14.0 |
| | | 2361 | 21.2 |
| untreated silica gel | | 324 | 5.4 |
| | | 460 | 8.5 |
| | | 685 | 18.0 |
| | | 971 | 21.5 |
| | | 2361 | 18.6 |

Figure 3:
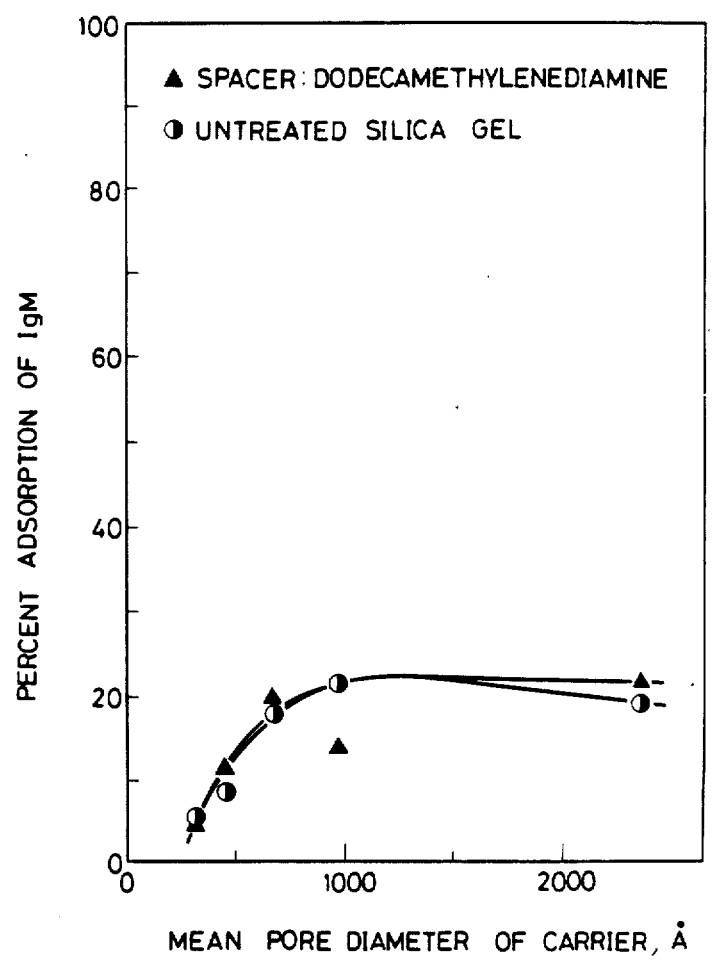
FIGS. 3 and 4 are diagrams illustrating percent IgM adsorption as a function of average pore diameter of carriers having sulfathiazole heterocylic compound attached thereto.
Figure 4:
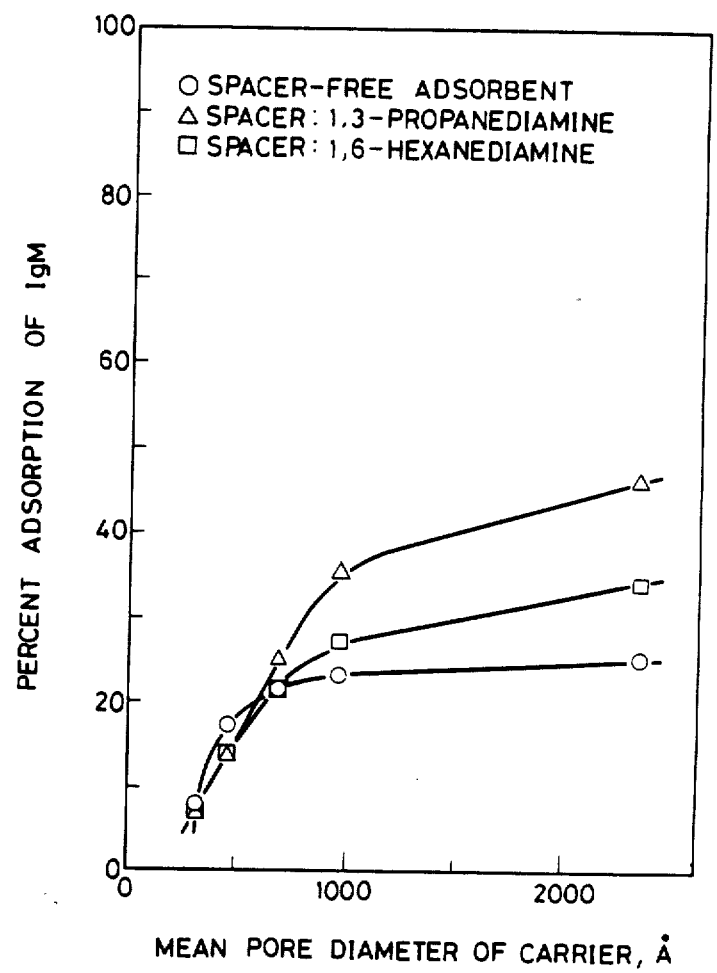

As evident from Table 2 and FIGS. 3 and 4, more efficient adsorption and removal of IgM was achieved when 1,3-propanediamine and 1,6-hexanediamine were used as a spacer, particularly when 1,3-propanediamine was used.

Further, the data indicate that average particle diameters of 900 Å or more results in higher adsorption.

EXAMPLE 2 AND COMPARATIVE EXAMPLE 2

The procedure of Example 1 and Comparative Example 1 was repeated using normal human plasma instead of bovine plasma and heterocyclic compounds as shown in Table 3. An adsorption test was carried out to determine the percent adsorption of IgM by the adsorbents.

The results are shown in Table 3.

TABLE 3

| (Normal human plasma) | | | |
|---|---|---|---|
| Heterocyclic compound | Spacer | Carrier average pore diameter, Å | IgM adsorption |
| Examples | | | |
| sulfathiazole | 1,3-propanediamine | 906 | 100.0 |
| sulfathiazole | 1,3-propanediamine | 2361 | 92.0 |
| sulfathiazole | 1,6-hexanediamine | 906 | 94.1 |
| sulfathiazole | 1,6-hexanediamine | 2361 | 81.8 |
| sulfathiazole | 1,9-diaminononane | 906 | 100.0 |
| sulfathiazole | 1,9-diaminononane | 2361 | 59.3 |

TABLE 3-continued (Normal human plasma)

| Heterocyclic compound | Spacer | Carrier average pore diameter, Å | IgM adsorption |
|---|---|---|---|
| sulfamethizole | 1,6-hexanediamine | 906 | 78.3 |
| sulfamethizole | 1,6-hexanediamine | 2361 | 62.8 |
| sulfisomezole | 1,6-hexanediamine | 906 | 96.1 |
| sulfisomezole | 1,6-hexanediamine | 2361 | 83.8 |
| sulfisomezole | 1,9-diaminononane | 906 | 82.6 |
| sulfisomezole | 1,9-diaminononane | 2361 | 72.9 |
| Comparative Examples | | | |
| sulfathiazole | — | 906 | 79.4 |
| sulfathiazole | — | 2361 | 50.5 |
| sulfathiazole | dodecamethylenediamine | 906 | 35.3 |
| sulfathiazole | dodecamethylenediamine | 2361 | 31.0 |
| sulfathiazole | p-phenylenediamine | 906 | 73.5 |
| sulfathiazole | p-phenylenediamine | 2361 | 33.3 |
| untreated silica gel | | 906 | 76.5 |
| untreated silica gel | | 2361 | 59.0 |
| sulfamethizole | — | 906 | 60.9 |
| sulfamethizole | — | 2361 | 38.8 |
| sulfamethizole | dodecamethylenediamine | 906 | 27.1 |
| sulfamethizole | dodecamethylenediamine | 2361 | 23.8 |
| sulfamethizole | p-phenylenediamine | 906 | 56.4 |
| sulfamethizole | p-phenylenediamine | 2361 | 25.6 |
| sulfisomezole | — | 906 | 79.3 |
| sulfisomezole | — | 2361 | 62.1 |
| sulfisomezole | dodecamethylenediamine | 906 | 43.4 |
| sulfisomezole | dodecamethylenediamine | 2361 | 38.1 |
| sulfisomezole | p-phenylenediamine | 906 | 80.7 |
| sulfisomezole | p-phenylenediamine | 2361 | 41.0 |

As evident from Table 3, more efficient adsorption and removal of IgM was achieved when 1,3-propanediamine, 1,6-hexanediamine, and 1,9-diaminononane were used as a spacer, particularly when 1,3-propanediamine was used.

Substantially equivalent results were obtained when other heterocyclic compounds such as sulfapyridine, sulfadiazine, sulfisomidine, 2-thiouracil, luminol, and isonicotinic acid hydrazide were used.

BENEFITS OF THE INVENTION

The immunoglobulin adsorbent of the present invention wherein a diamine compound having the general formula:

$$NH_2(CH_2)_nNH_2$$

wherein n is an integer having a value of 3 to 9, such as 1,3-propanediamine, 1,6-hexanediamine, or 1,9-diaminononane is attached to a hydroxyl-containing water-insoluble carrier through a silane coupling agent or a derivative thereof and a heterocyclic compound is attached to the diamine through a difunctional reagent can selectively and efficiently adsorb and remove such proteins as immunoglobulins and immune complexes which are pathogenic substances in body fluid. Since the ligand is a relatively low molecular weight organic compound, the adsorbent can be readily sterilized without an error.

The present invention is usable in general applications where body fluid is depurated through adsorption for regeneration, and particularly effective in the treatment of polyclonal immunoglobulin M diseases (chronic hepatitis, cirrhosis, scleroderma, lymphomatosis, congenital rubella, congenital syphilis, congenital toxoplasmosis, tripanosomal infectious disease, subacute sclerosing panencephalitis, and other diseases where IgM increases), immune complex diseases (glomerulonephritis, systemic lupus erythematosus (SLE), chronic rheumatism, periarteritis nodosa, serum sickness, chronic graft-versus-host disease (GVHD), and other diseases where immune complexes increase), and transplantation (AOB incompatibility bone-marrow transplantation, etc.).

The immunoglobulin adsorbents of the present invention is not only used as a therapeutic instrument by filling a vessel therewith, but also useful as members for the isolation, purification, and detection of such proteins as immunoglobulins and immune complexes.

We claim:

1. An apparatus for adsorbing an immunoglobulin in a body fluid comprising
   a vessel having an inlet and an outlet for passing body fluid therethrough,
   an adsorbent for an immunogloblin charged in said vessel, said adsorbent comprising a hydroxyl-containing water-insoluble carrier to which a diamine compound having the general formula:

$$NH_2(CH_2)_nNH_2$$

wherein n is an integer having a value of 3 to 9 is attached through a silane coupling agent or a derivative thereof, a heterocyclic compound being attached to the amine through a difunctional reagent, and
   means for preventing the adsorbent from flowing out of said vessel.

2. The adsorbent of claim 1 wherein the diamine compound is selected from the group consisting of 1,3-propanediamine, 1,6-hexanediamine, and 1,9-diaminononane.

3. The adsorbent of claim 1 wherein the diamine compound has a length of from about 5 to about 20 angstrom.

4. The adsorbent of claim 1 wherein the total length of the silane coupling agent, the diamine compound, and the heterocyclic compound ranges from about 40 to about 55 angstrom.

5. The adsorption apparatus of claim 1 wherein said means comprises a filter disposed in said vessel.

6. An adsorbent for an immunoglobulin comprising a hydroxyl-containing water-insoluble carrier to which a diamine compound having the general formula:

$$NH_2(CH_2)_nNH_2$$

wherein n is an integer having a value of 3 to 9 is attached through a silane coupling agent or a derivative thereof, wherein a heterocyclic compound is attached to the diamine through a difunctional reagent, wherein the total length of the silane coupling agent, the diamine compound, the difunctional reagent and the heterocyclic compound ranges from about 40 to about 55 angstrom.

7. The adsorbent of claim 6 wherein the diamine compound is selected from the group consisting of 1,3-propanediamine, 1,6-hexanediamine, and 1,9-diaminononane.

8. The adsorbent of claim 6 wherein the diamine compound has a length of from about 5 to about 20 angstrom.

9. The adsorbent of claim 6 wherein said difunctional reagent is a difunctional reagent capable of bonding amino groups with each other and said heterocyclic compound has an amino group or an amino group incorporated therein.

10. The adsorbent of claim 6 wherein said heterocyclic compound is a sulfa drug in the form of a sulfonamide.

11. The adsorbent of claim 6 wherein said silane coupling agent is selected from the group consisting of γ-glycidoxypropyltrimethoxysilane, γ-glycidoxypropylmethyldiethoxysilane, β-(3,4-epoxycyclohexyl)ethyltrimethoxysilane, γ-aminopropyltriethoxysilane, and N-β(aminoethyl)-γ-aminopropyltrimethoxysilane.

12. The adsorbent of claim 6 wherein said difunctional reagent is selected from the group consisting of dialdeydes, bisepoxides, alkylimide esters, and diisocyanates.

13. The adsorbent of claim 12 wherein said difunctional reagent is glutaraldehyde.

14. The adsorbent of claim 6 wherein said water-insoluble carrier is comprised of a porous inorganic material predominantly comprising silicon dioxide and having a silanol group.

15. The adsorbent of claim 14 wherein said water-insoluble carrier is in the form of particles having a particle diameter in the range between 0.05 mm and 5 mm.

16. The adsorbent of claim 14 wherein said water-insoluble carrier has a mean pore diameter between 1000 angstrom and 5000 angstrom.

17. An adsorbent for an immunoglobulin comprising a hydroxyl-containing water-insoluble carrier to which a diamine compound having the general formula:

$$NH_2(CH_2)_nNH_2$$

wherein n is an integer having a value of 3 to 9 is attached through a silane coupling agent or a derivative thereof, wherein a heterocyclic compound is attached to the diamine through a difunctional agent, wherein said heterocyclic compound is a sulfa drug, said sulfa drug being selected from the group consisting of sulfathiazole, sulfamethizole and sulfisomezole.

* * * * *

UNITED STATES PATENT AND TRADEMARK OFFICE
CERTIFICATE OF CORRECTION

PATENT NO. : 4,705,628
DATED : November 10, 1987
INVENTOR(S) : Yuichi YAMAMOTO and Tadashi SAMESHIMA It is certified that error appears in the above-identified patent and that said Letters Patent is hereby corrected as shown below:

Claim 2, line 1, delete "adsorbent" and insert --adsorption apparatus--.

Claim 3, line 1, delete "adsorbent" and insert --adsorption apparatus--.

Claim 4, line 1, delete "adsorbent" and insert --adsorption apparatus--.

Claim 12, line 3, delete "dialdeydes" and insert --dialdehydes--.

Signed and Sealed this

Fourteenth Day of June, 1988

Attest:

DONALD J. QUIGG

Attesting Officer      Commissioner of Patents and Trademarks